(12) United States Patent (10) Patent No.: US 7,930,927 B2
Cooper et al. (45) Date of Patent: Apr. 26, 2011

(54) TRANSDERMAL PORTABLE ALCOHOL MONITOR AND METHODS FOR USING SUCH

(75) Inventors: Larry T. Cooper, Longmont, CO (US); Timothy D. Waters, Boulder, CO (US); Donald A. Melton, Boulder, CO (US); Victor Rompa, Westminster, CO (US)

(73) Assignee: BI Incorporated, Boulder, CO (US)

( * ) Notice: Subject to any disclaimer, the term of this patent is extended or adjusted under 35 U.S.C. 154(b) by 375 days.

(21) Appl. No.: 12/041,765

(22) Filed: Mar. 4, 2008

(65) Prior Publication Data

US 2008/0216561 A1 Sep. 11, 2008

Related U.S. Application Data

(60) Provisional application No. 60/893,264, filed on Mar. 6, 2007.

(51) Int. Cl.
*G01N 33/487* (2006.01)
(52) U.S. Cl. ...................................... 73/53.01
(58) Field of Classification Search .................. 73/53.01
See application file for complete search history.

(56) References Cited

U.S. PATENT DOCUMENTS

| | | | |
|---|---|---|---|
| 3,966,579 A * | 6/1976 | Chang et al. | 204/406 |
| 4,724,427 A | 2/1988 | Carroll | |
| 4,843,377 A | 6/1989 | Fuller et al. | |
| 4,857,893 A | 8/1989 | Carroll | |
| 4,918,432 A | 4/1990 | Pauley et al. | |
| 5,220,919 A | 6/1993 | Phillips et al. | |
| 5,627,520 A | 5/1997 | Grubbs et al. | |
| 5,889,474 A | 3/1999 | LaDue | |
| 5,936,529 A | 8/1999 | Reisman et al. | |
| 5,944,661 A * | 8/1999 | Swette et al. | 600/345 |
| 6,014,080 A | 1/2000 | Layson, Jr. | |
| 6,072,396 A | 6/2000 | Gaukel | |
| 6,130,620 A | 10/2000 | Pinnow et al. | |
| 6,774,797 B2 | 8/2004 | Freathy et al. | |
| 6,992,582 B2 | 1/2006 | Hill et al. | |
| 7,123,141 B2 | 10/2006 | Contestabile | |
| 7,386,152 B2 | 6/2008 | Rowe et al. | |
| 7,611,461 B2 * | 11/2009 | Hawthorne et al. | 600/300 |
| 7,636,047 B1 * | 12/2009 | Sempek | 340/572.8 |
| 2002/0140559 A1 | 10/2002 | Zhou et al. | |
| 2003/0210149 A1 | 11/2003 | Reisman et al. | |
| 2004/0236199 A1 | 11/2004 | Hawthorne et al. | |

(Continued)

FOREIGN PATENT DOCUMENTS

WO WO 2005019977 3/2005

(Continued)

OTHER PUBLICATIONS

Marques, et al. "Evaluation of Transdermal Alcohol Devices" Pacific Institute for Research and Evaluation, NHTSA Task Order DTNH22-02-D-95121, pp. 1-31.

(Continued)

*Primary Examiner* — Hezron Williams
*Assistant Examiner* — Rodney T Frank
(74) *Attorney, Agent, or Firm* — Hamilton, DeSanctis & Cha

(57) ABSTRACT

Various embodiments of the present invention provide alcohol monitoring devices, and methods for using such. As one example, an alcohol monitoring device is disclosed that includes a device body, an alcohol sensor, and a liquid cartridge. The alcohol sensor is associated with the device body, and relies on a liquid supply to perform an alcohol measurement on a subject. The liquid cartridge is replaceably coupled to the device body and provides the liquid supply to the alcohol sensor.

22 Claims, 9 Drawing Sheets

U.S. PATENT DOCUMENTS

| | | | |
|---|---|---|---|
| 2005/0250440 A1 | 11/2005 | Zhou et al. | |
| 2006/0202836 A1 | 9/2006 | Hawthorne et al. | |
| 2006/0202837 A1 | 9/2006 | Hawthorne et al. | |
| 2008/0108370 A1* | 5/2008 | Aninye | 455/456.1 |

FOREIGN PATENT DOCUMENTS

| | | |
|---|---|---|
| WO | WO 2005038590 | 4/2005 |
| WO | WO 2006108077 | 10/2006 |

OTHER PUBLICATIONS

Marques, et al., "Evaluating Transdermal Alcohol Measuring Devices" Pacific Institute for Research and Evaluation, NHTSA, Nov. 2007, pp. 1-96.

Pollard, et al. "Review of Technology to Prevent Alchol-Impaired Crashes" U.S Department of Transportation NHTSA, DOT HS 810 833, Sep. 2007, pp. 1-108.

Pollard, et al., "Vehicle Technologies to Prevent Crashes Involving Alcohol-Impaired Drivers" The Volpe Center, Aug. 11, 2006, pp. 1-28.

Ratcliffe, "www.stltoday.com," Dec. 26, 2007, pp. 1-2.

Robertson, et al., "Alcohol Monitoring: A Primer for Criminal Justice Professionals" Traffic Injury Research Foundation, Oct. 2006, pp. 1-34.

Shellem, "SCRAM Can Alert Probation Officers if Someone's Been Drinking", The Patriot-News, Nov. 25, 2007, pp. 1-3.

\* cited by examiner

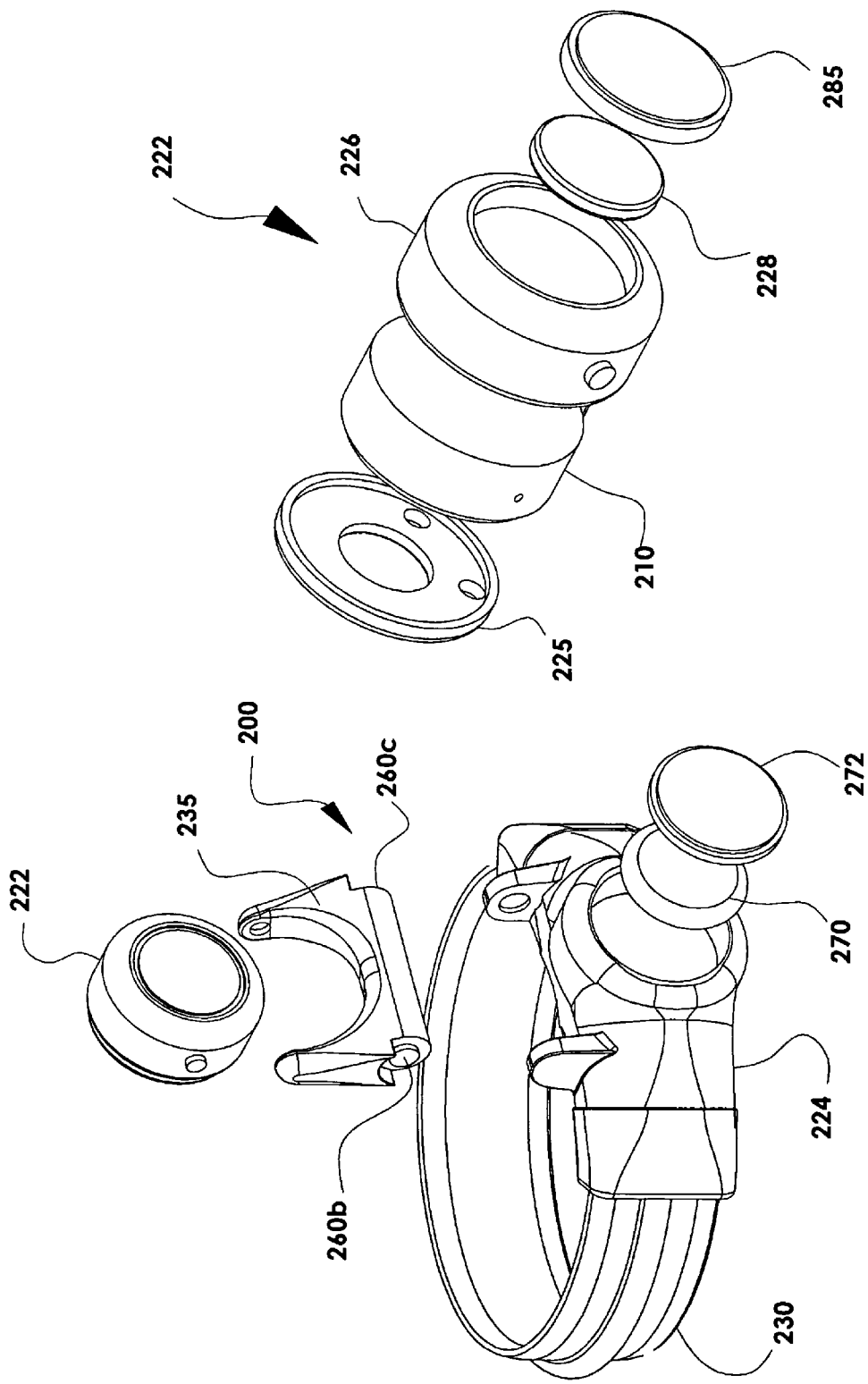

TRANSDERMAL PORTABLE ALCOHOL MONITOR AND METHODS FOR USING SUCH

CROSS REFERENCE TO RELATED APPLICATION

The present application claims priority to (i.e., is a non-provisional of) U.S. Pat. App. No. 60/893,264 entitled "Systems and Methods for Alcohol Detection", and filed Mar. 6, 2007 by Cooper et al. The entirety of the aforementioned application is incorporated herein by reference for all purposes.

BACKGROUND OF THE INVENTION

The present invention is related to tracking devices, and in particular to tracking devices capable of monitoring alcohol consumption in human subjects.

Large numbers of individuals are currently housed in prisons. This represents a significant cost to society both in terms of housing expense and wasted productivity. To address this concern, house arrest systems have been developed for use by less violent offenders. This allows the less violent offender to be monitored outside of a traditional prison system and allows the offender an opportunity to work and interact to at least some degree in society. The same approach is applied to paroled prisoners allowing for a monitored transition between a prison atmosphere and returning to society.

In some cases, it is not practical to parole an offender because they suffer from an alcohol addiction that may lead to the same activity that lead to their original incarceration. Present approaches to monitor alcohol consumption costly, time consuming and in some cases, impractical. In other cases, the terms of an individual's parole may include a requirement that the individual abstain from the use of alcohol, but monitoring adherence to such terms is costly and time consuming. In yet other circumstances, it may be possible that an individual could avoid incarceration altogether if they agree to abstain from the use of alcohol. Again, assuring adherence to such terms is at best costly and time consuming.

Giner Inc. of Newton, Mass. has developed a product that includes a transdermal alcohol monitor with a strap allowing it to be placed around the leg of an individual being monitored. Such an approach offers some hope in portable alcohol monitoring. Unfortunately, the strap has to be maintained relatively tight to assure reasonable reading. Such is not always possible due to the movement of the individual being monitored. In some cases, such movement reduced the accuracy of any readings and in some cases results in an inability to rely on the readings. Further, such a device is not easily serviceable and may be susceptible to tampering by the monitored individual.

Thus, for at least the aforementioned reasons, there exists a need in the art for more advanced approaches, devices and systems for detecting alcohol usage by an individual.

BRIEF SUMMARY OF THE INVENTION

The present invention is related to tracking devices, and in particular to tracking devices capable of monitoring alcohol consumption in human subjects.

Some embodiments of the present invention provide portable alcohol monitoring devices. Such devices include a device body, an alcohol sensor, and a liquid cartridge. The alcohol sensor is associated with the device body, and relies on a liquid supply to perform an alcohol measurement on a subject. The liquid cartridge is replaceably coupled to the device body and provides the liquid supply to the alcohol sensor. In some instances of the aforementioned embodiments, the liquid cartridge is filled with water. In one particular instance, the water is distilled, de-ionized water. The liquid cartridge may be, but is not limited to, a cylindrical cartridge, or a cubical cartridge.

In some instances of the aforementioned embodiments, the alcohol monitoring devices further include a securing device that is operable to secure the device body to the subject. In various instances of the aforementioned embodiments, the alcohol sensor is incorporated in the device body, and a force element presses the alcohol sensor toward the subject. As one example, the force element may be a spring and the alcohol sensor may be coupled to the device body via a bellows. In other instances, the device body includes an electronics body and a sensor body with the sensor body encasing the alcohol sensor and being attached to the electronics body via a torsion hinge. In such cases, the torsion hinge operates to press the alcohol sensor toward the subject.

In some instances of the aforementioned embodiments, the liquid cartridge is coupled to the body device using tamper resistant hardware. In some cases, the tamper resistant hardware is designed such that it is damaged upon replacement of the liquid cartridge. As just some examples, the tamper resistant hardware may be, but is not limited to, a tamper resistant cap, and a tamper resistant screw. In particular instances of the aforementioned embodiments, the device further includes a proximity detector that is operable to detect whether the device body is within a desired proximity of the subject. Further, in some instances of the aforementioned embodiments, the device further includes at least one tamper sensor that is operable to detect unauthorized tampering with the device.

Other embodiments of the present invention provide portable alcohol monitoring devices that include a device body, an alcohol sensor that is associated with the device body, a securing device that is operable to secure the device body to the subject, and a force element that is operable to press the alcohol sensor toward the subject.

Yet other embodiments of the present invention provide methods for maintaining alcohol monitoring equipment. Such methods include providing a portable alcohol monitoring device having a device body, an alcohol sensor, and a liquid cartridge. The alcohol sensor is associated with the device body, and relies on a liquid supply to perform an alcohol measurement on a subject. The liquid cartridge is replaceably coupled to the device body and provides the liquid supply to the alcohol sensor. The methods further include removing a tamper resistant hardware element, and in doing so damaging the tamper resistant hardware element. Further, the methods include removing and replacing the liquid cartridge, and replacing the tamper resistant hardware. In some cases, the replacing the liquid cartridge includes refilling an existing liquid cartridge and replacing it, while in other cases replacing the liquid cartridge includes using a different liquid cartridge.

This summary provides only a general outline of some embodiments according to the present invention. Many other objects, features, advantages and other embodiments of the present invention will become more fully apparent from the following detailed description, the appended claims and the accompanying drawings and figures.

BRIEF DESCRIPTION OF THE DRAWINGS

A further understanding of the various embodiments of the present invention may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

FIGS. 2a-2c depict another alcohol monitoring device in accordance with different embodiments of the present invention;

DETAILED DESCRIPTION OF THE INVENTION

Figure 1A:
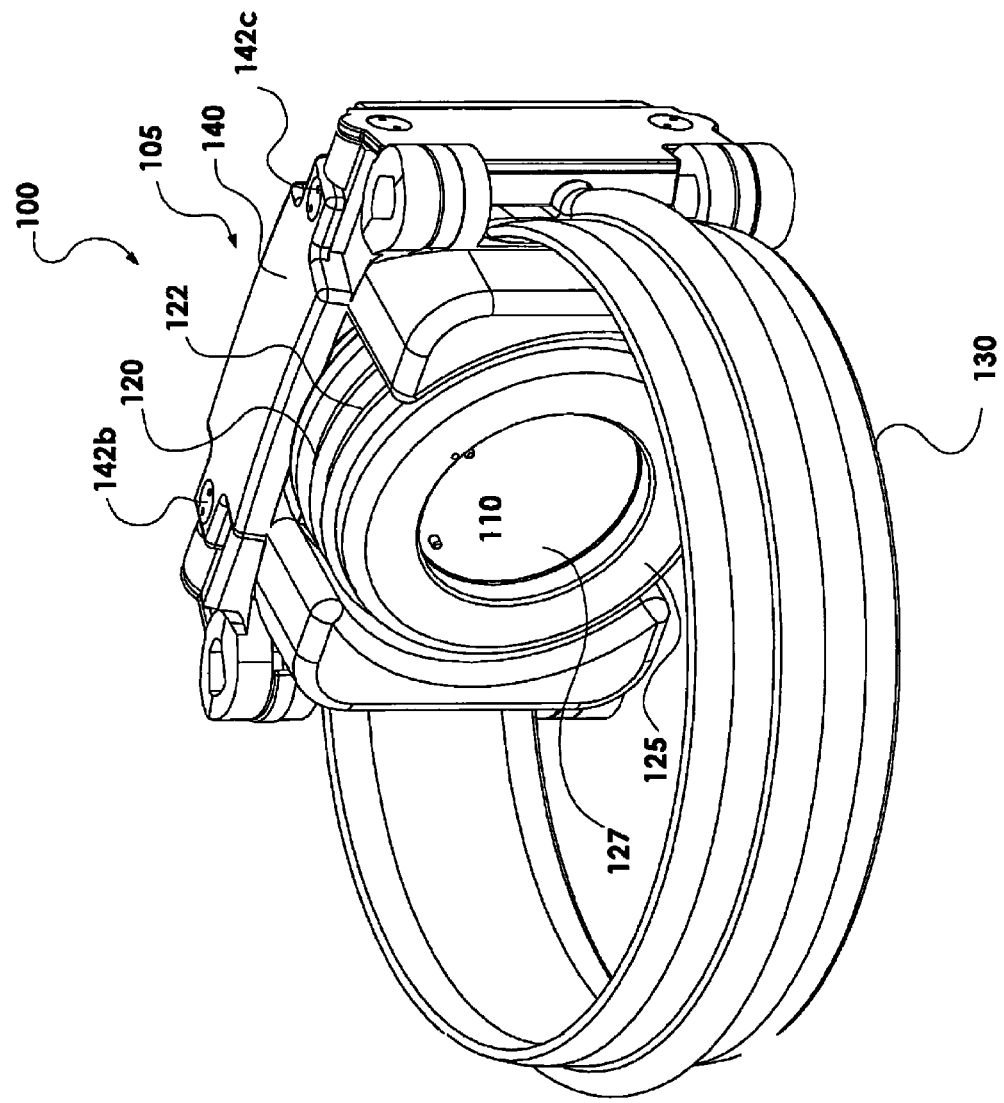
FIGS. 1a-1d depict an alcohol monitoring device in accordance with various embodiments of the present invention.

The present invention is related to tracking devices, and in particular to tracking devices capable of monitoring alcohol consumption in human subjects.

Some embodiments of the present invention provide portable alcohol monitoring devices. Such devices include a device body, an alcohol sensor, and a liquid cartridge. As sued herein, the phrase "device body" is used in its broadest sense to mean a portion of a device including hardware for performing one or more functions. In some cases, the device body may be a case holding one or more functional elements, while in other cases, the device body includes two or more cases with each holding functional elements. In the aforementioned embodiments, the alcohol sensor is associated with the device body, and relies on a liquid supply to perform an alcohol measurement on a subject. The liquid cartridge is replaceably coupled to the device body and provides the liquid supply to the alcohol sensor. As used herein, the phrase "liquid cartridge" is used in its broadest sense to mean any container capable of holding a liquid.

In some instances of the aforementioned embodiments, the alcohol monitoring devices further include a securing device that is operable to secure the device body to the subject. In various instances of the aforementioned embodiments, the alcohol sensor is incorporated in the device body, and a force element presses the alcohol sensor toward the subject. As used herein, the phrase "force element" is used in its broadest sense to mean an element capable of providing some level of force to an object. As one example, the force element may be a spring and the alcohol sensor may be coupled to the device body via a bellows. As another example, the force element may be a torsion spring.

In some instances of the aforementioned embodiments, the liquid cartridge is filled with water. In one particular instance, the water is distilled, de-ionized water. The liquid cartridge may be, but is not limited to, a cylindrical cartridge, or a cubical cartridge. As used herein, the phrase "cubicle cartridge" is used in its broadest sense to mean any container having the general shape of a cube where the length of the container sides are not necessarily equal. Similarly, the phrase "cylindrical cartridge" is used in its broadest sense to mean any container having the general shape of a cylinder.

In some instances of the aforementioned embodiments, the liquid cartridge is coupled to the body device using tamper resistant hardware. As used herein, the phrase "tamper resistant hardware" is used in its broadest sense to mean any hardware element that provides some indication of tampering when it has been tampered with. In some cases, the tamper resistant hardware is designed such that it is damaged upon replacement of the liquid cartridge. Such damage may be in some cases, irreparable damage. As just some examples, the tamper resistant hardware may be, but is not limited to, a tamper resistant cap, and a tamper resistant screw.

Turning to FIG. 1a, an alcohol monitoring device 100 is depicted in accordance with various embodiments of the present invention. Alcohol monitoring device 100 includes a body 105 that includes various monitoring and/or tracking circuitry. Such circuitry may include, but is not limited to, alcohol detection circuitry, location circuitry and/or tamper circuitry. The alcohol detection circuitry may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. In addition, the monitoring circuitry may include transmission and/ore reception circuitry as is known in the art for transmitting information from alcohol monitoring device 100, and receiving information at alcohol monitoring device 100. The information transmitted by alcohol monitoring device may include an indication of whether a monitored individual has been consuming alcohol and to what level the consumption has progressed. The information may be transmitted to a central monitoring station where it is monitored. Based on the disclosure provided herein, one of ordinary skill in the art will recognize a variety of information that may be transmitted to/from alcohol monitoring device, a variety of uses of such information, and a variety of transmission methods and protocols that may be utilized in accordance with different embodiments of the present invention. The tamper circuitry may include any circuitry known in the art that are capable of determining whether any interference with alcohol monitoring device 100. Such interference may include, but is not limited to, blocking the alcohol sensor, interfering with the transmission of information to/from alcohol monitoring device 100, and/or cutting an attachment securing alcohol monitoring device 100 to the human subject. Such tamper sensors may include, but are not limited to, a proximity sensor that is able to determine whether alcohol monitoring device 100 is within reasonable proximity of the skin of the monitored individual. Based on the disclosure provided herein, one of ordinary skill in the art will recognize a variety of tamper sensors that may be used in conjunction with the various embodiments of the present invention. The various sensors included in alcohol measurement device 100 may include, but are not limited to, blockage sensor indicating that no gas is being allowed to reach an included alcohol sensor, a temperature sensor, a proximity sensor indicating that alcohol measurement device is within a defined range of the monitored individual, a skin probe capable of measuring skin resistance as an indication of whether alcohol measurement device is still being worn by the monitored individual, and/or the like. Based on the disclosure provided herein, one of ordinary skill in the art will recognize a variety of other sensors that may be used in relation to different embodiments of the present invention.

Body 105 is attachable to a human subject using a strap 130. Strap 130 is attachable using some sort of buckle or other connector as are known in the art. In some cases, strap 130 includes a continuity detector (not shown) imbedded therein. In one particular embodiment of the present invention, the continuity detector is an electrical conductor extending around strap 130 and making a connection in body 105. As such, when strap 130 is either unbuckled or cut, the electrical conductor is broken and the break is detected by circuitry within body 105. In other particular embodiments of the present invention, the continuity detector is a fiber optic conductor that may similarly be used to determine whether strap 130 has been unbuckled or cut. Based on the disclosure provided herein, one of ordinary skill in the art will appreciate a variety of straps and associated securing devices that may be used in accordance with different embodiments of the present invention to secure body 105 to a monitored individual. In one particular embodiment, strap 130 includes an outer case with an imbedded fiber optic continuity conductor and banding for added strength.

Body 105 includes an alcohol sensor 110 that is maintained at a controlled distance from the monitored individual's skin by a dermal seal 125 and a telescoping housing 120. The combination of dermal seal 125 and telescoping housing 120 create a reasonably stable gas region 127 between alcohol sensor 110 and the monitored individual's skin. Dermal seal 125 may be, for example, a set of foam pads that are capable of creating a reasonable seal with the skin of a monitored individual, and yet are comfortable to the monitored individual. In particular instances, the foam pads are made of closed cell foam that allows for positioning and ergonomic fit. Based on the disclosure provided herein, one of ordinary skill in the art will recognize other materials that may be used to form dermal seal 125 in accordance with the various embodiments of the present invention. Telescoping housing 120 is operable to press alcohol sensor 110 near the skin of the monitored individual. Because of this, alcohol sensor 110 is maintained at a reasonably constant distance from the monitored individual's skin even when the individual is moving. This promotes better readings from alcohol sensor 110 without the need to tighten strap 130 beyond a comfortable point. As more fully described below, in one embodiment of the present invention, telescoping housing 120 includes an expandable bellows 122 that allows for movement of alcohol sensor 110 relative to body 105, and a spring (not shown) that presses alcohol sensor 110 and dermal seal 125 away from body 105 and toward the human subject's skin. In particular instances of the aforementioned embodiments, expandable bellows 122 is made of rubber, while in other instances it is formed of some type of flexible plastic. Based on the disclosure provided herein, one of ordinary skill in the art will recognize a variety of materials that may be used to create expandable bellows 122 in accordance with various embodiments of the present invention.

Body 105 also includes a water tight compartment 140 that includes a replaceable liquid cartridge (not shown) and electronics (not shown) for operating alcohol monitoring device 100. Water tight compartment 140 is accessible by removing tamper resistant screws 142. In some embodiments of the present invention, tamper resistant screws 142 may require a special tool for removal to minimize the possibility that a monitored individual will open water tight compartment 140 and attempt to interfere or otherwise control the operation of alcohol monitoring device 100. In other embodiments of the present invention, tamper resistant screws 142 are only one way devices allowing for the closure of water tight compartment 140. Opening water tight compartment 140 requires the destruction of tamper resistant screws 142. When water tight compartment 140 is to be resealed, a new pair of tamper resistant screws is required. In this way, any unauthorized opening of water tight compartment 140 will be readily apparent. In some cases, the aforementioned approach may be combined with a sensor (not shown) that indicates that water tight compartment 140 is open. Thus, when water tight compartment 140 is opened an error message may be prepared and transmitted to a central monitoring location by alcohol monitoring device 100. This would allow for detection of any tampering within a reasonable period of when the tampering occurred, and additional scrutiny of the monitored individuals behavior during that period.

Figure 1B:
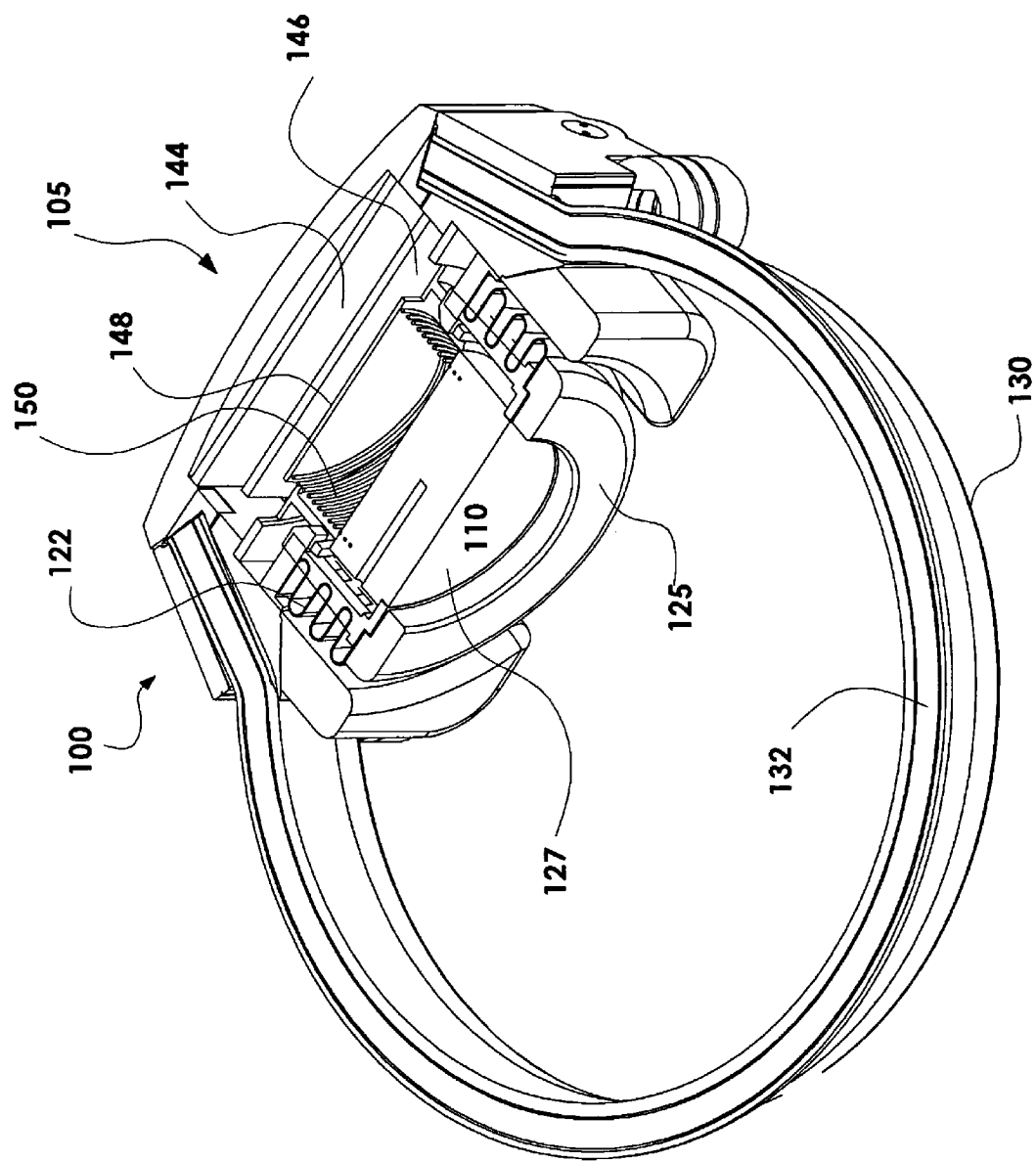

Turning to FIG. 1b, a cut away view of alcohol monitoring device 100 is presented. Of interest, expandable bellows 122 are shown as having a serpentine shape that allows for extension away from and toward body 105. Also shown is a spring 150 that provides the force for moving alcohol sensor 110 toward the skin of the monitored individual. In addition, a fiber optic conductor 132 is shown extending through strap 130. The interior of water tight compartment 140 is shown with an area 144 to hold a replaceable liquid cartridge (not shown), and an area 146 for electronic circuitry (not shown) for controlling the various operations of alcohol monitoring device 100. A bulk head 148 provides an area for spring 150 to press against and forms the outer wall of water tight compartment 140.

Figure 1C:
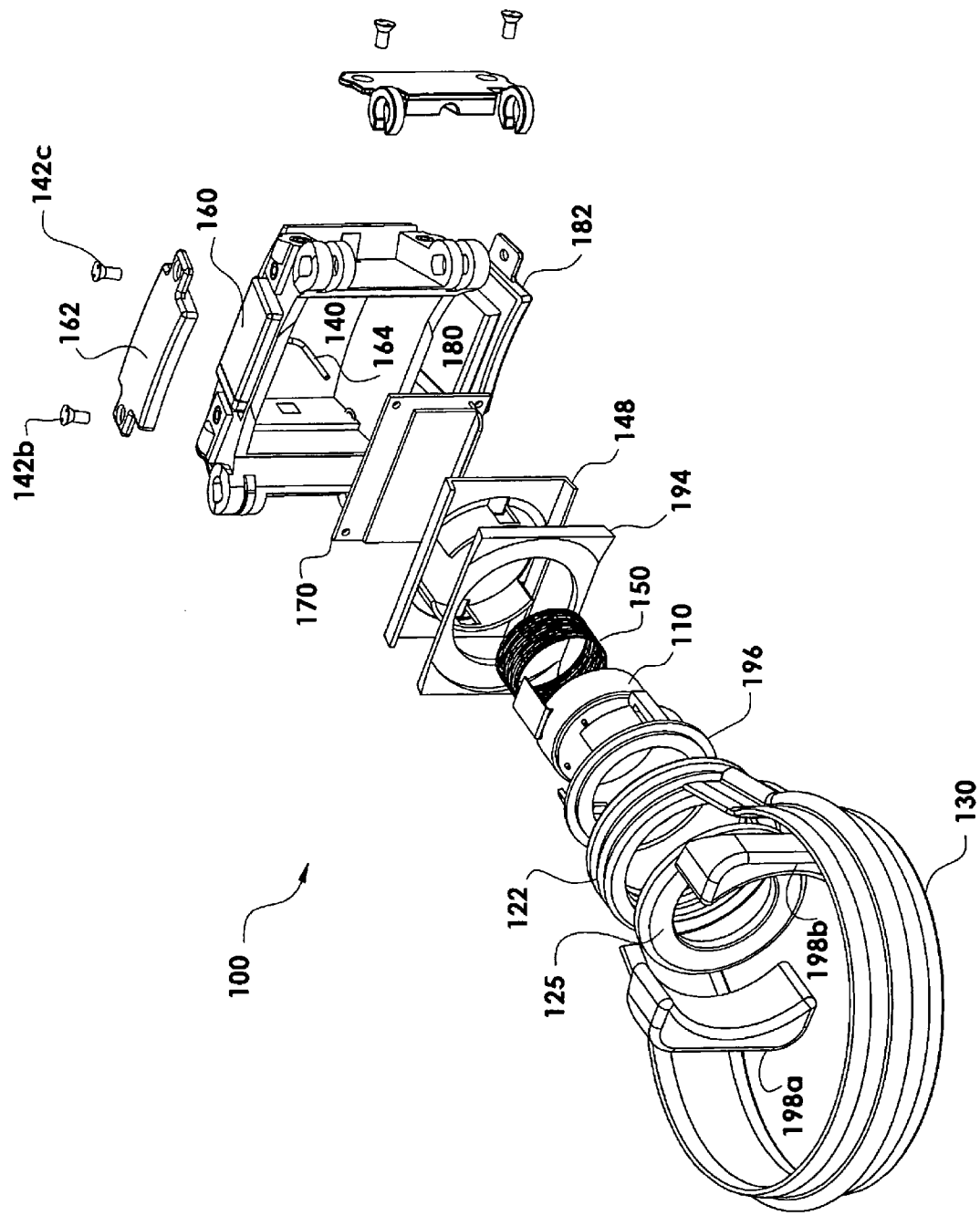

Turning to FIG. 1c, an exploded view of alcohol monitoring device 100 is presented. As shown, a battery 180 is connected to body 105 using a removable connector plate 182. Battery 180 provides power to operate alcohol monitoring device 100. A replaceable liquid cartridge 160 is placed in water tight compartment 140 and held in place by an outer plate 162 that is held in place by tamper resistant screws 142. In one embodiment of the present invention, liquid cartridge 160 is a plastic container that includes a supply of water used to operate alcohol sensor 110. Use of such a liquid cartridge allows for easy replenishment of water. In some cases, the water is distilled water that is not always readily available in the field. By using such a replaceable liquid cartridge, quick and easy replenishment of any desired liquid is rendered more manageable. A feed line 164 allows for dispersing liquid from liquid cartridge 160 to alcohol sensor 110. In some cases, feed line 164 is implemented as a wick capable of transporting a defined saturation of liquid.

An electronic circuit board 170 holds electronics responsible for controlling the various operations of alcohol monitoring device 100, and is connected in water tight compartment 140. A case cover 194 and bulk head 148 separates water tight compartment 140 from alcohol sensor 110. Spring 150 presses alcohol sensor 110 away from body 105 and toward the skin of the monitored individual. A sensor carriage 196 captures alcohol sensor 110 and allows it to move in and out and stay within a desired range of the monitor individual's skin. Expandable bellows 122 contact dermal seal 125 that includes foam pads 198 on opposite sides.

Figure 1D:
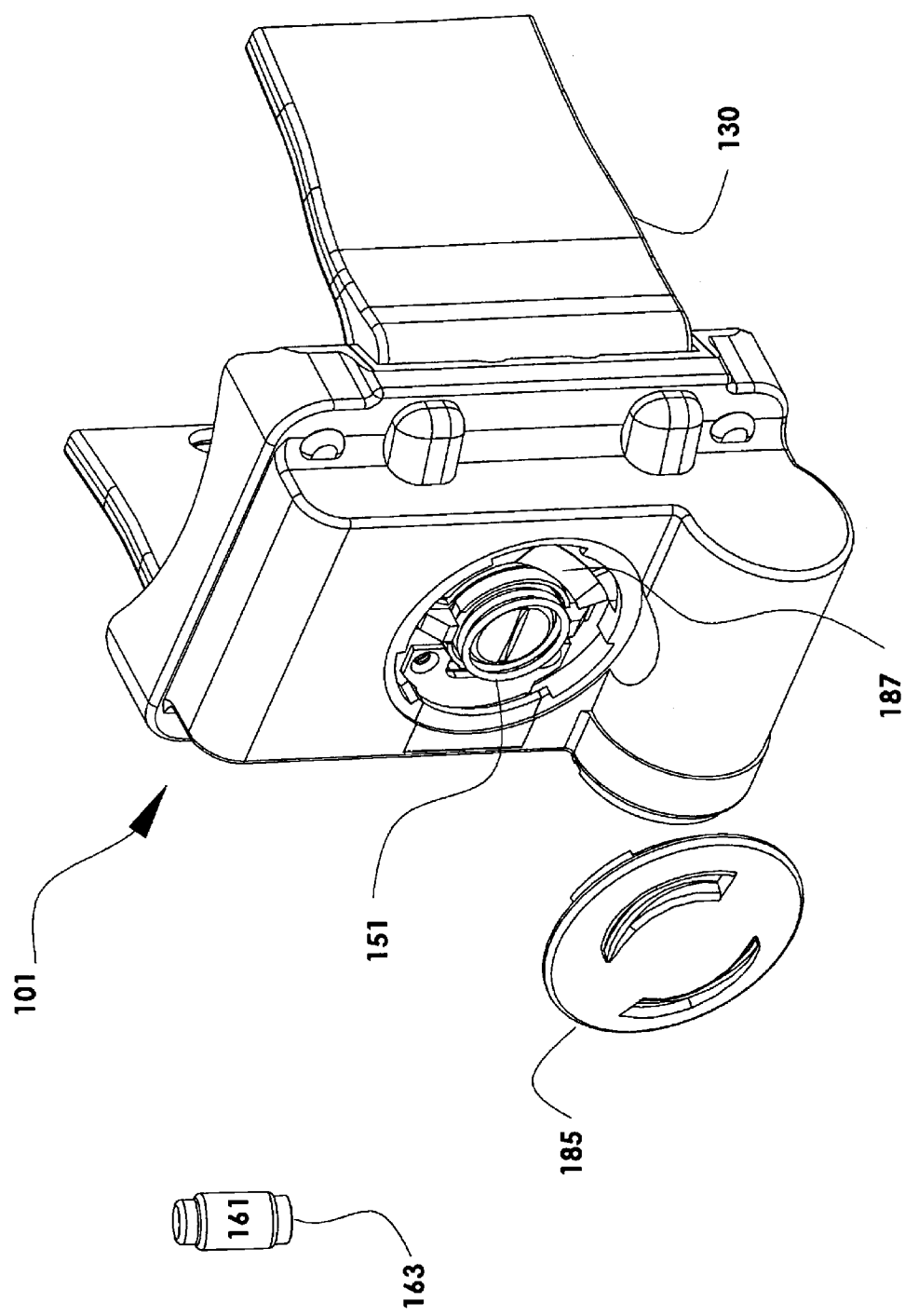

Turning to FIG. 1d, an alternative embodiment of a body 101 that may be used in place of body 105 is depicted. As shown, body 101 includes an opening in which a spring 151 is placed. Spring 151 is used similar to spring 150 to press an alcohol sensor (not shown) away from body 101 and toward the skin of the monitored individual. A cylindrical liquid cartridge 161 may be placed inside of spring 151. One end of cylindrical cartridge 161 includes a wick that assures a defined range of moisture saturation in proximity of the alcohol sensor. Cylindrical cartridge 161 is designed to be replaceable in the field. In one embodiment of the present invention, cylindrical cartridge 161 is a plastic container that includes a supply of water used to operate alcohol sensor 110. Use of such a replaceable cartridge allows for easy replenishment of water. In some cases, the water is distilled water that is not always readily available in the field. By using such a replaceable liquid cartridge, quick and easy replenishment of any desired liquid is rendered more manageable.

Spring 150 and cylindrical cartridge 161 are held in place by tamper resistant cap 185. Tamper resistant cap 185 is installed by placing it onto body 101 over spring 150 and cylindrical cartridge 161 and turned a quarter turn. When initially pressed onto body 101, tamper resistant cap 185 causes a flat spring 187 to press inward. Upon turning tamper resistant cap 185, it locks into body 101 with flat spring 187 extending away from body 101 into a void on tamper resistant cap 185. In the extended condition, flat spring 187 precludes twisting tamper resistant cap 185 to open body 101. Thus, the only way to access cylindrical cartridge 161 is to break tamper resistant cap 185. Thus, any unauthorized access to body 101 will be readily apparent. When replacing cylindrical cartridge 161 with a full cartridge, tamper resistant cap 185 is broken and a new cylindrical cartridge 161 is inserted in place of the replaced cartridge. A new tamper resistant cap 185 is then installed.

Figure 2A:
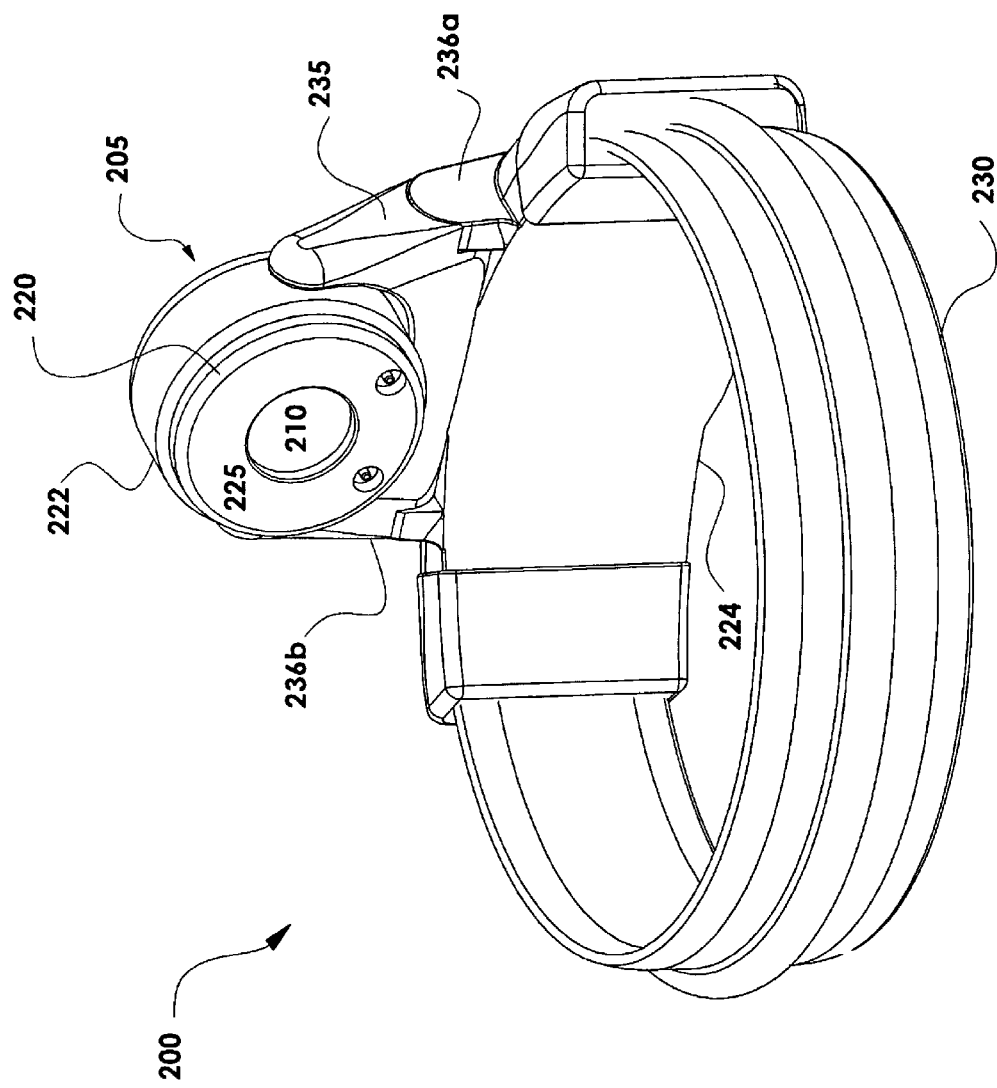

Turning to FIG. 2a, an alcohol monitoring device 200 is depicted in accordance with various embodiments of the present invention. Alcohol monitoring device 200 includes a body 205 that includes various monitoring and/or tracking circuitry. Such circuitry may include, but is not limited to, alcohol detection circuitry, location circuitry and/or tamper circuitry. The alcohol detection circuitry may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. In addition, the monitoring circuitry may include transmission and/ore reception circuitry as is known in the art for transmitting information from alcohol monitoring device 200, and receiving information at alcohol monitoring device 200. The tamper circuitry may include any circuitry known in the art that are capable of determining whether any interference with alcohol monitoring device 200.

Body 205 is attachable to a human subject using a strap 230. Strap 230 is attachable using some sort of buckle or other connector as are known in the art. In some cases, strap 230 includes a continuity detector (e.g., either an electrical conductor or optical conductor) imbedded therein. As such, when strap 230 is either unbuckled or cut, the conductor is broken and the break is detected by circuitry within body 205. In one particular embodiment, strap 230 includes an outer case with an imbedded fiber optic continuity conductor and banding for added strength.

Body 205 includes an alcohol sensor body 222 and an electronics body 224. Electronics body 224 houses a battery and electronic circuitry responsible for the various operations of alcohol monitoring device 200. Alcohol sensor body 222 holds a sensor housing 225 that articulates to stay in contact with the skin of a monitored individual. In some cases, alcohol sensor body 222 may include a spring and an expandable bellows similar to that discussed above in relation to alcohol monitoring device 100. Alcohol sensor body 222 operates to hold an alcohol sensor 210 within a defined range of the skin of a monitored individual. This assures that more accurate readings are possible.

Alcohol sensor body 222 is held in relation to electronics body 224 by a support bracket 235 connected via torsion hinges 236 on either side. Torsion hinges 236 operate to force alcohol sensor body 222 toward the center of strap 230, thus causing alcohol sensor 210 to be disposed nearer the skin of the monitored individual. In one particular embodiment of the present invention, torsion hinges 236 are spring loaded hinges providing only a minimal amount of pressure sufficient to keep sensor body 222 in contact the appropriate skin.

Turning to FIG. 2b, an exploded view of alcohol monitoring device 200 is provided. In particular, support bracket 235 including torsion hinges 236 is shown disconnected from both alcohol sensor body 222 and electronics body 224. In addition, a tamper resistant cap 272 is removed from electronics body 224 revealing a battery 270. Tamper resistant cap 272 is installed by placing it onto electronics body 224 over battery 270 and turned a quarter turn. Tamper resistant cap 272 may be installed over a flat spring similar to that discussed above in relation to tamper resistant cap 185. Such an approach requires damaging tamper resistant cap 272 whenever it is removed rendering any tampering evident. Alternatively, or in addition, tamper resistant cap 272 may require a specialized tool for removal to minimize the possibility that a monitored individual will tamper with alcohol monitoring device 200. Further, in some cases, the aforementioned approaches may be combined with a sensor (not shown) that indicates that tamper resistant cap 272 has been removed. Thus, when tamper resistant cap 272 is removed, an error message may be prepared and transmitted to a central monitoring location by alcohol monitoring device 200. This would allow for detection of any tampering within a reasonable period of when the tampering occurred, and additional scrutiny of the monitored individuals behavior during that period.

Turning to FIG. 2c, an exploded view of alcohol sensor body 222 is shown. In this embodiment, alcohol sensor body 222 includes an outer casing 226 into which alcohol sensor 210 is placed and secured therein using a face plate 225 that doubles as a dermal seal. In some cases, dermal seal 225 is made of a plastic material sturdy enough to maintain alcohol sensor 210 in place and pliable enough when placed in relation to human skin to render a reasonable seal. Based on the disclosure provided herein, one of ordinary skill in the art will recognize a variety of materials that may be used to create dermal seal 225 in accordance with different embodiments of the present invention.

Outer casing 226 additionally houses a replaceable liquid cartridge 228 that is maintained in place by a tamper resistant cap 285. A wick or liquid feed mechanism traverses an inner wall 228 of outer casing to allow liquid from liquid cartridge 228 to reach alcohol sensor 210. In one embodiment of the present invention, replaceable liquid cartridge 228 is a plastic container that includes a supply of water used to operate alcohol sensor 210. Use of such a liquid cartridge allows for easy replenishment of water. In some cases, the water is distilled water that is not always readily available in the field. By using such a replaceable liquid cartridge, quick and easy replenishment of any desired liquid is rendered more manageable.

Tamper resistant cap 285 is installed by placing it onto outer casing 226 over liquid cartridge 228 and turned a quarter turn. Tamper resistant cap 285 may be installed over a flat spring similar to that discussed above in relation to tamper resistant cap 185. Such an approach requires damaging tamper resistant cap 285 whenever it is removed rendering any tampering evident. Alternatively, or in addition, tamper resistant cap 285 may require a specialized tool for removal to minimize the possibility that a monitored individual will tamper with alcohol monitoring device 200. Further, in some cases, the aforementioned approaches may be combined with a sensor (not shown) that indicates that tamper resistant cap 285 has been removed. Thus, when tamper resistant cap 285 is removed, an error message may be prepared and transmitted to a central monitoring location by alcohol monitoring device 200. This would allow for detection of any tampering within a reasonable period of when the tampering occurred, and additional scrutiny of the monitored individuals behavior during that period.

Figure 3B:
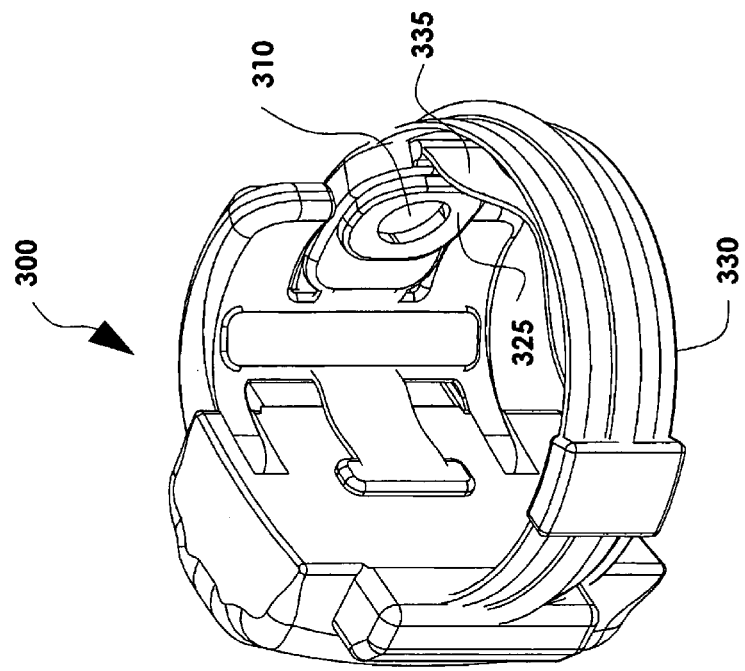
FIGS. 3a-3b depict yet another alcohol monitoring device in accordance with yet other embodiments of the present invention.
Figure 3A:
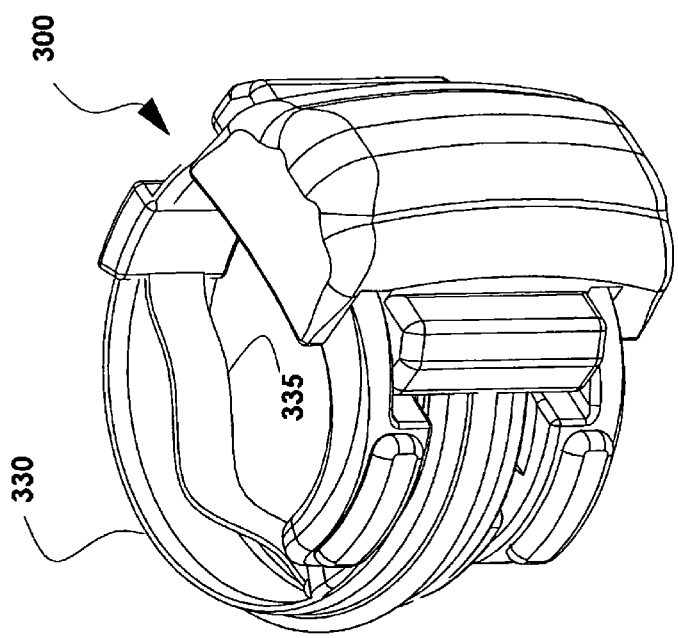

Turning to FIGS. 3a-3b, two views of another alcohol monitoring device 300 is depicted in accordance with yet other embodiments of the present invention. As shown, alcohol monitoring device 300 includes an alcohol sensor 310 that is maintained a desired distance from the skin of a monitored individual by a dermal seal 325. Alcohol sensor 310 is maintained in proximity to the skin though use of a flexible sub-strap 335 that is more flexible than a main strap 330. Flexible sub-strap 335 is attached to a sensor assembly including alcohol sensor 310 and dermal seal 325. This allows alcohol sensor 310 to be maintained near the skin of the monitored individual without requiring that the entire alcohol monitoring device 300 be maintained in the same proximity. This allows for greater comfort and improved alcohol measurement results.

Figure 4:
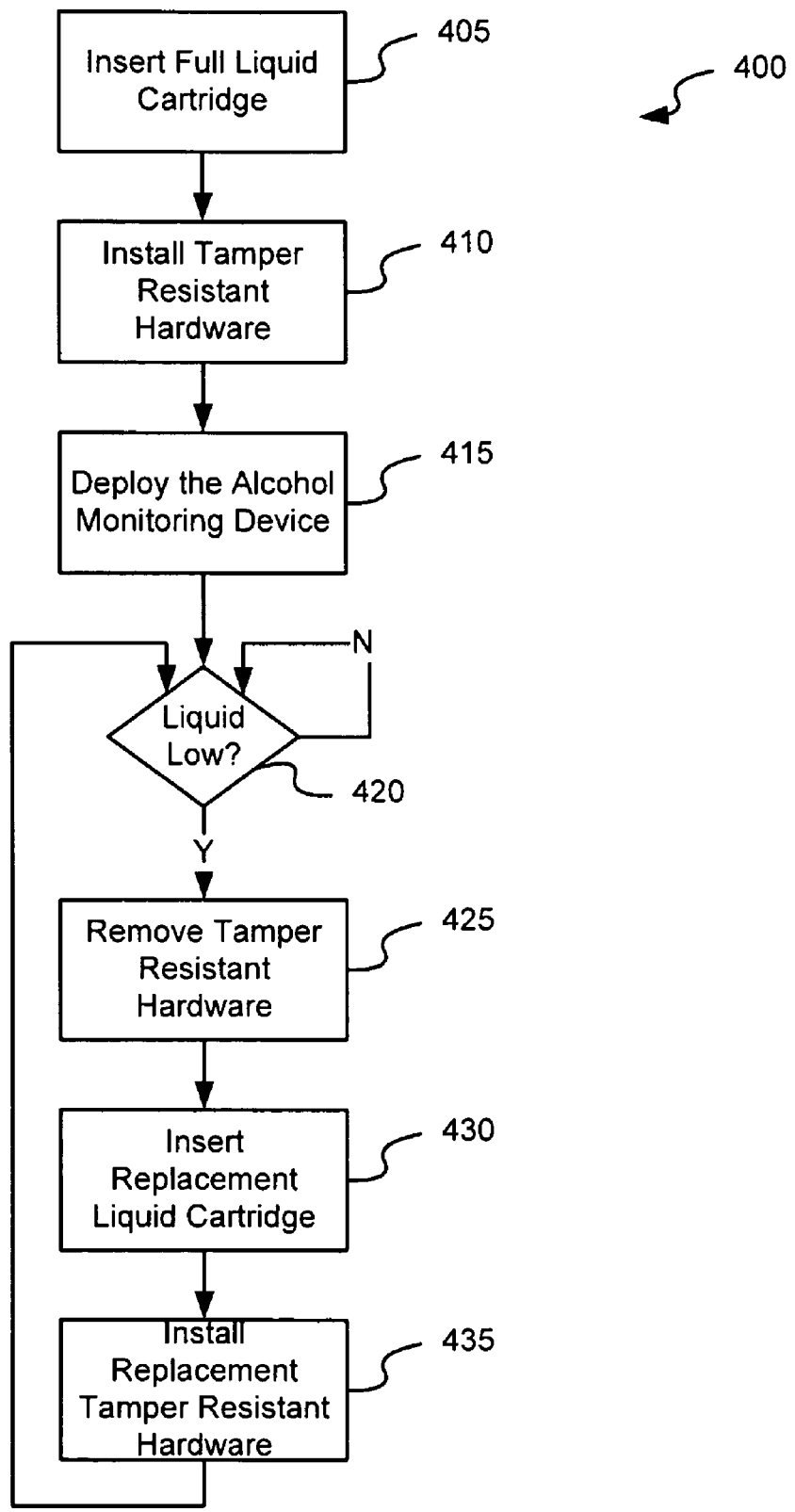
FIG. 4 is a flow diagram depicting a process for servicing an alcohol monitoring device in accordance with some embodiments of the present invention.

Turning to FIG. 4, a flow diagram 400 depicts a process for servicing an alcohol monitoring device in accordance with some embodiments of the present invention. Following flow diagram 400, a full liquid cartridge is initially installed in an alcohol measuring device (block 405). This process may include, for example, inserting a new liquid cartridge into an opening of the alcohol monitoring device designed to hold the cartridge. Such a liquid cartridge may include, for example, a supply of distilled, de-ionized water that is designed to support operation of the alcohol monitoring device for a desired range of time. Inclusion of a larger cartridge allows for greater extension of device operation between maintenance intervals.

Once the liquid cartridge is installed (block 405), tamper resistant hardware is installed over the liquid cartridge to hold it in place (block 410). This may include, but is not limited to, installing a plate using tamper resistant screws or covering the opening through which the liquid cartridge is inserted using a tamper resistant cap. Further, it may include turning on a sensor that indicates that a tamper has occurred if such circuitry is available. The alcohol monitoring device may then be deployed (block 415). This may include securing the alcohol measuring device to a monitored individual.

During deployment, it may be determined whether the liquid in the installed liquid cartridge is low (block 420). This may include, for example, determining that the installed liquid sensor has been in for a certain time period and that it needs to be replaced. In other cases, the alcohol monitoring device may be able to detect when the liquid in the liquid cartridge is low. In such a case, a sensor message may be transmitted to a central monitoring system. In either case, where it is determined that the liquid level is potentially or actually low, the alcohol monitoring device is serviced. Such service may include summoning the monitored individual to a prescribed location where the device is serviced. This may be a scheduled service time corresponding, for example, to a visit with a parole officer. Alternatively, a technician or parole officer may visit the monitored individual and service the alcohol monitoring device in situ. Use of a cartridge based approach to the liquid reservoir makes such servicing possible.

The servicing includes removing the tamper resistant hardware holding the liquid cartridge in place (block 425). This may include destroying part of the hardware which will need to be replaced with new parts. A new liquid cartridge is then inserted in place of the removed liquid cartridge rendered accessible by removing the tamper resistant hardware (block 430), and replacement tamper resistant hardware is installed to hold the replacement liquid cartridge in place (block 435).

Figure 5:
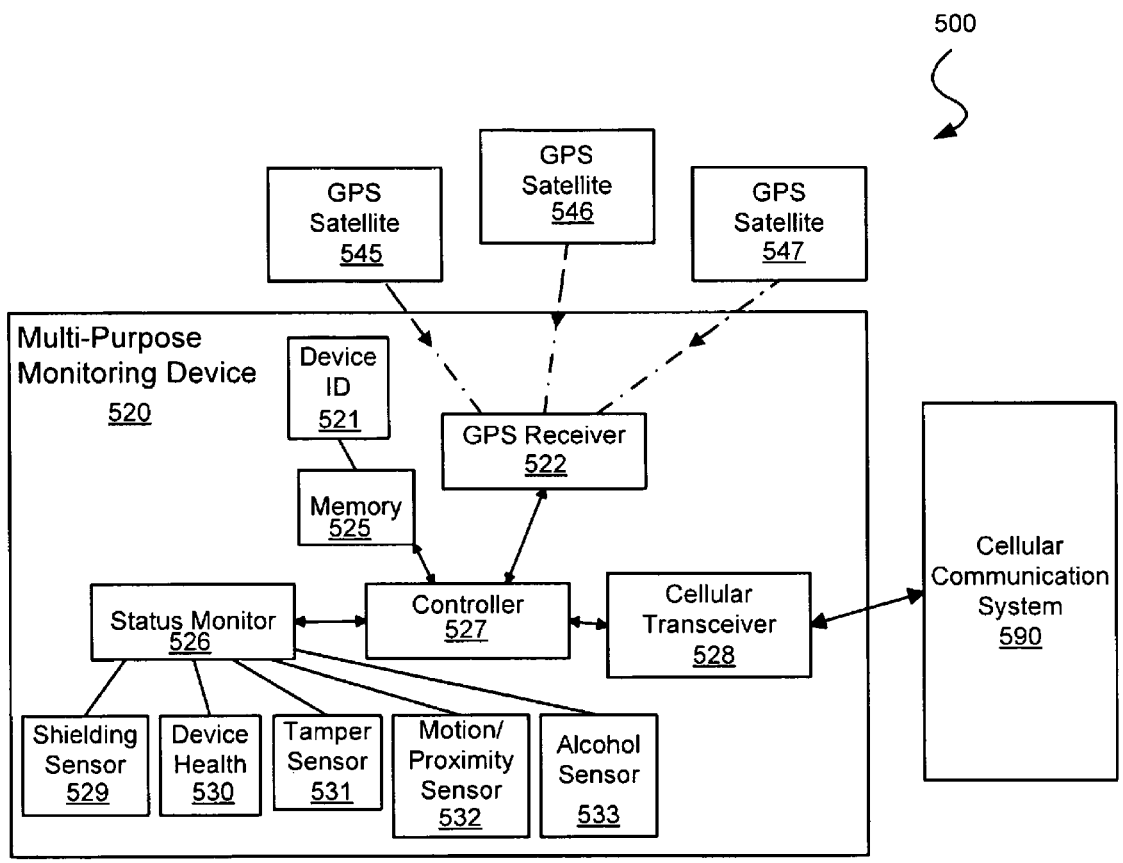
FIG. 5 depicts the block diagram of a monitoring device capable of monitoring subject location as well as alcohol usage.

Turning to FIG. 5, a tracking and alcohol monitoring system 500 is depicted in accordance with some embodiments of the present invention. Tracking and monitoring system 500 includes a multi-purpose monitoring device 520 that is capable of both tracking an individual and monitoring alcohol consumption of the individual. This device can be incorporated in the electronics of the devices of FIGS. 1, 2 and 3. As shown, multi-purpose monitoring device 520 includes a GPS receiver 522 that is capable of receiving GPS information from GPS satellites 345, 346, and 347 respectively. GPS receiver 322 is useful for determining physical locations, i.e. whenever GPS receiver 322 is powered-on, and also as long as receiving sufficient GPS satellites signal transmissions.

Multi-purpose monitoring device 520 includes a device ID 521 that may be maintained in a memory 525, and thus is accessible by a controller 527. Controller 57 is able to interact with GPS receiver 522 and memory 525 at times for storing and generating records of successively determined GPS locations. Controller 527 may be, but is not limited to, a microprocessor, microcontroller or other device known in the art that is capable of executing software or firmware instructions. Memory 525 may be any type of memory known in the art such as, for example, a EEPROM or RAM memory.

Controller 527 of subject device 520 at times functions in conjunction with a cellular transceiver 528 to send and receive data and signals through cellular communication system 590. This link at times is useful for passing information and/or control signals between a central monitoring system (not shown) and multi-purpose monitoring device 520. The information transmitted may include, but is not limited to, location information, alcohol information, and information about the status of multi-purpose monitoring device 520. Based on the disclosure provided herein, one of ordinary skill in the art will recognize a variety of information that may be transferred via cellular communication system 590.

Various embodiments of multi-purpose monitoring device 520 include a variety of sensors capable of determining the status of multi-purpose monitoring device 520, and of the individual associated therewith. For example, a status monitor 526 may include one or more of the following subcomponents: a set of shielding sensors 529 that are capable of determining whether subject device is being shielded from receiving GPS signals and/or if GPS jamming is ongoing, a set of device health indicators 530, a tamper sensor 531 capable of determining whether unauthorized access to subject device 520 has occurred or whether subject device 520 has been removed from an associated human subject, a motion/proximity sensor 532 capable of determining whether subject device 520 is moving and/or whether it is within proximity of an individual associated with multi-purpose monitoring device 520, and/or an alcohol sensor 533 such as that described herein. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into subject device 520 according to various different instances and/or embodiments of the present invention. In some cases, transmission of alcohol data is done at one frequency, and house arrest information is transmitted at another frequency. In one particular embodiment of the present invention, house arrest information (i.e., location information) is transmitted using a 300 MHz-320 MHz, and alcohol information is transmitted using a 902 MHz-928 MHZ band. The higher frequency band allows for transmission of substantial amounts of information, while the lower frequency band allows for transmission of smaller amounts of data.

In conclusion, the present invention provides for novel systems, devices, and methods for monitoring alcohol consumption by human subjects. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A portable alcohol monitoring device, the device comprising:
    a device body including a sensor body and an electronics body;
    an alcohol sensor, wherein the alcohol sensor relies on a liquid supply to perform an alcohol measurement on a subject, wherein the alcohol sensor is associated with the sensor body, and wherein the sensor body is coupled to the electronics body via a force element that is operable to press the alcohol sensor toward the subject and away from the electronics body; and
    a liquid cartridge; wherein the liquid cartridge is replaceably coupled to the device body and provides the liquid supply to the alcohol sensor.

2. The device of claim 1, wherein the device further includes:
    a securing device, wherein the securing device is operable to secure the device body to the subject.

3. The device of claim 1, wherein the alcohol sensor is incorporated in the device body, and wherein a force element presses the alcohol sensor toward the subject.

4. The device of claim 3, wherein the force element is a spring.

5. The device of claim 4, wherein the alcohol sensor is coupled to the device body via a bellows.

6. The device of claim 1, wherein the liquid cartridge is filled with water.

7. The device of claim 1, wherein the water is distilled, de-ionized water.

8. The device of claim 1, wherein the liquid cartridge is selected from a group consisting of: a cylindrical cartridge, and a cubical cartridge.

9. The device of claim 1, wherein the liquid cartridge is coupled to the body device using tamper resistant hardware.

10. The device of claim 9, wherein the tamper resistant hardware is damaged upon replacement of the liquid cartridge.

11. The device of claim 9, wherein the tamper resistant hardware is selected from a group consisting of: a tamper resistant cap, and a tamper resistant screw.

12. The device of claim 1, wherein the device further includes:
    a proximity detector, wherein the proximity detector is operable to detect whether the device body is within a desired proximity of the subject.

13. The device of claim 1, wherein the device further includes at least one tamper sensor, and wherein the at least one tamper sensor is operable to detect unauthorized tampering with the device.

14. The device of claim 1, wherein the force element includes a torsion hinge.

15. A portable alcohol monitoring device, the device comprising:
    a device body including a sensor body and an electronics body;
    an alcohol sensor, wherein the alcohol sensor relies on a liquid supply to perform an alcohol measurement on a subject, wherein the alcohol sensor is incorporated in the sensor body, and wherein the sensor body is coupled to the electronics body via a force element that that is operable to press the alcohol sensor toward the subject and away from the electronics body;
    an alcohol sensor, wherein the alcohol sensor is associated with the sensor body;
    a securing device, wherein the securing device is operable to secure the device body to the subject; and
    a force element, wherein the force element is operable to press the alcohol sensor toward the subject and away from the electronics body.

16. The device of claim 15, wherein the alcohol sensor relies on a liquid supply to perform an alcohol measurement on a subject, and wherein the device further includes:
    a liquid cartridge; wherein the liquid cartridge is replaceably coupled to the device body and provides the liquid supply to the alcohol sensor.

17. The device of claim 15, wherein the alcohol sensor is incorporated in the device body, and wherein the force element is a spring.

18. The device of claim 15, wherein a liquid cartridge is coupled to the body device using tamper resistant hardware.

19. The device of claim 15, wherein the force element includes a torsion hinge.

20. A portable monitoring device, the device comprising:
    a device body including a sensor body and a main body, wherein the sensor body is operable to include a transdermal alcohol sensor, and wherein the sensor body is coupled to the main body via a force element;
    a securing device, wherein the securing device is operable to secure the device body to a subject; and
    wherein the force element is operable to press the sensor body toward the subject and away from the main body.

21. The portable monitoring device of claim 20, wherein the force element includes a torsion hinge.

22. The portable monitoring device of claim 20, the device further including:
    the alcohol sensor, wherein the alcohol sensor relies on a liquid supply to perform an alcohol measurement on a subject; and
    a liquid cartridge; wherein the liquid cartridge is replaceably coupled to the sensor body and provides the liquid supply to the alcohol sensor.

* * * * *